(12) United States Patent
Cao

(10) Patent No.: US 6,579,357 B1
(45) Date of Patent: Jun. 17, 2003

(54) BIOC1 PIGMENT

(75) Inventor: Paul Cao, Ossining, NY (US)

(73) Assignee: Engelhard Corporation (JP)

( * ) Notice: Subject to any disclaimer, the term of this patent is extended or adjusted under 35 U.S.C. 154(b) by 0 days.

(21) Appl. No.: 10/143,902

(22) Filed: May 14, 2002

(51) Int. Cl.⁷ .................................................. C09C 1/22
(52) U.S. Cl. ........................ 106/459; 106/415; 106/456; 106/479
(58) Field of Search ................................ 106/415, 456, 106/479

(56) References Cited

U.S. PATENT DOCUMENTS

| | | |
|---|---|---|
| 2,995,459 A | 8/1961 | Soloway |
| 3,822,141 A | 7/1974 | Kaufman |
| 3,980,491 A | 9/1976 | Eberts |
| 5,149,369 A | 9/1992 | Eberts et al. |
| 5,344,488 A | 9/1994 | Reynders et al. |
| 5,958,125 A | 9/1999 | Schmid et al. |

Primary Examiner—Mark L. Bell
Assistant Examiner—Shalie Manlove
(74) Attorney, Agent, or Firm—Dickstein, Shapiro, Morin & Oshinsky, LLP

(57) ABSTRACT

A bismuth oxychloride effect pigment exhibiting improved light stability has a discontinuous coating of hydrous iron oxide on the crystals of the bismuth oxychloride. The pigment is prepared by growing the bismuth oxychloride crystals, adding a hydrolyzable iron salt thereto and then hydrolyzing the iron salt.

18 Claims, No Drawings

BIOCl PIGMENT

BACKGROUND OF THE INVENTION

Effect pigments, which are also known as pearlescent pigments or nacreous pigments, are well known. These are laminar or plate-like pigments which impart a pearly or nacreous luster into objects on which or in which they are used. The known effect pigments include naturally occurring substances such as pearlescence, a mixture of guanine and hypoxanthine which is obtained from the scales of fish, as well as various synthetic materials. The effect pigments which are most often encountered commercially are titanium dioxide-coated mica and iron oxide-coated mica. Other synthetic effect pigments which have been developed for both cosmetic and industrial use include materials such as bismuth oxychloride and lead carbonate.

Bismuth oxychloride has been used as an effect pigment in a number of fields. It is used, for instance, as a pigment in cosmetics, such as nail enamels and lipsticks, and it is also used to pigment plastics and paints. The coating of a bismuth oxychloride-coated mica pigment with hydrous titanium hydroxide is described in U.S. Pat. No. 3,980,491 and the coating of a metal oxide-coated bismuth oxychloride with zinc oxide is described in U.S. Pat. No. 5,344,488. Coprecipitation of bismuth oxychloride and titanium dioxide on a mica substrate is described in U.S. Pat. No. 3,822,141. U.S. Pat. No. 2,995,459 discloses combining a synthetic pearlescent substrate, including bismuth oxychloride with insoluble metallic compound coloring agents such as the sulfides, molybdates, tungstates, xanthates and dithiazones of Cd, Mn, Co, Fe and Sb but cautions that formation of a randomly deposited unoriented coating destroys the luster of the pigment. U.S. Pat. No. 5,958,125 discloses a pigment based on a substrate, which can be bismuth oxychloride, having at least one layer packet of a colorless coating having a refractive index of 1.8 or less and a reflecting absorbing coating, of which iron oxides are examples. The iron oxide coated product, however, cannot be dried without causing clumping of the iron oxide in the coating. This is not a problem when the pigment is employed in a paste but is, of course, significant in other uses.

In order to extend the range of applications, bismuth oxychloride pigments have been coated with such materials as 2-hydroxy benzophenones and rare earth metals in order to impart ultraviolet stability or weather fastness properties to the effect pigment. See, U.S. Pat. No. 5,149,369. The result of coating a BiOCl pigment itself, however, is that some of the natural luster and brightness is desired to improve the light stability of the bismuth oxychloride while achieving a better brightness and dispersability of the product.

It is accordingly the object of the present invention to provide an improved bismuth oxychloride effect pigment with a better appearance (brightness) and greater dispersability and to provide a method for producing such a pigment.

SUMMARY OF THE INVENTION

The present invention relates to an improved bismuth oxychloride effect pigment and a process for its production. More particularly, the invention relates to an improved bismuth oxychloride effect pigment having a discontinuous surface coating of hydrous iron oxide which can be produced by hydrolyzing a soluble bismuth salt in the presence of chloride followed by coating the resulting crystals with hydrous iron oxide. The iron coating generates a decorative effect with colors ranging from gold to dark brown (champagne) depending on the amount of iron, while imparting greatly improved ultraviolet light stability, preventing photo darkening.

DESCRIPTION OF THE INVENTION

In accordance with the present invention, bismuth oxychloride crystals are grown in any conventional manner and are then discontinuously coated with hydrous iron oxide.

Bismuth oxychloride crystals are typically produced by combining a soluble bismuth compound with a source of chloride under acid conditions. While any soluble bismuth compound can be used, the material which is most often employed is bismuth nitrate. The bismuth salt is usually employed in the form of an aqueous acidic solution to prevent premature hydrolysis and precipitation of insoluble bismuth compounds. For this purpose, the solution usually contains a compatible mineral or other strong acid. Hydrochloric acid and a mixture of hydrochloric and nitric acids are particularly convenient since they serve as a source of the chloride ions which are used to form the bismuth oxychloride. The bismuth compound is hydrolyzed by maintaining the acidity within desired limits, usually about pH 1, by adding a suitable base to neutralize acid which forms during the hydrolysis reaction. The base most often used is an alkali metal hydroxide, particularly sodium hydroxide, but other soluble sources of hydroxyl ions, such as a strongly basic amine or a base precursor such as urea, can also be used.

The preparation of the bismuth oxychloride crystals is generally effected at a temperature between about 50° C. and 100° C. and more preferably about 60–80° C. Usually the soluble bismuth salt solution and the base are pumped into an aqueous acidic reservoir. Any desired bismuth oxychloride crystal size can be realized by regulating the amount of the bismuth solution which is used.

To the resulting bismuth oxychloride crystals is added a hydrolyzable source of iron. Preferably, the iron is provided in the form of an aqueous solution of a water soluble iron salt such as ferric chloride and ferric sulphate. The pH of the resulting slurry is then adjusted such that the iron salt undergoes hydrolysis and becomes a coating on the surface of the bismuth oxychloride crystals. Any suitable base can be used to adjust the pH and as in the case of the hydrolysis of the bismuth compounds, an alkali metal hydroxide, particularly sodium hydroxide, can be used. The hydrous iron oxide is formed by changing the pH of the bismuth oxychloride environment so that it is in a range of about 2 to 4, and more preferably about 2.75–3.25. The hydrolysis of the iron can be effected at a temperature between ambient and about 100° C. and preferably at about 60 to 80° C.

The amount of the iron solution added to the bismuth oxychloride slurry depends on the desired color of the effect pigment. As the amount of the iron increases, the absorption color changes. In general, the amount of the iron salt added will range from about 1 to 70 weight percent depending on the desired color, preferably about 10 to 40 weight percent, based on the weight of the bismuth oxychloride crystals in the slurry. This results in the formation of a hydrous iron oxide coating on the bismuth oxychloride crystals in which the coating amounts to about 0.1 to 70 weight, preferably about 10 to 40 weight percent, of the total weight of the pigment. As a result of depositing the hydrous iron oxide before the bismuth oxychloride is isolated from the reaction mixture, a continuous coating is not formed. Therefore, the coating is not smooth and continuous but rather the hydrolyzed iron concentrates in a plurality of small clumps and thereby forms a discontinuous coating on the BiOCl. That, in turn, results in the inherent brightness of the BiOCl effect pigment continuing to be visible and being substantially retained. In addition, the discontinuous coating allows the final product to be dried without the iron oxide clumping.

At the end of the hydrous iron oxide precipitation, the resulting pigment is recovered from the solution in which it was formed in any convenient fashion. For example, the pigment can be filtered and then is preferably washed with water until substantially free of salt. Alternatively, a settling and decanting procedure can be employed. The pigment can be dried by heating or air dried, if desired, but temperatures which convert the hydrous iron oxide to iron oxide should be avoided.

The resulting hydrous iron oxide coated BiOCl effect pigment is thereafter processed in the conventional manner into various types of finished products. For example, the filter cake can be dried to produce a powdered product either with or without an added dispersing agent. Alternatively, the filter cake can be flushed with an oil such as castor oil or mineral oil, which causes the pigment originally wet with water to become a pigment wet with oil.

The resulting hydrous iron oxide coated bismuth oxychloride can be employed in the same manner as the previously known bismuth oxychloride effect pigments have been employed. For example, they can be used in cosmetics as well as paints and coatings. The plurality of crystals in the products made by the present inventive process have been found to be more homogeneous than conventional bismuth oxychloride effect pigments, combining brightness with enhanced light stability. This makes it possible to use the material in light colors of automotive paint and which also generates a liquid metal appearance.

Products of this invention have an unlimited use in all types of automotive and industrial paint applications, especially in the organic color coating and inks field where deep color intensity is required. For example, these pigments can be used in mass tone or as styling agents to spray paint all types of automotive and non-automotive vehicles. Similarly, they can be used on all clay/formica/wood/glass/metal/enamel/ceramic and non-porous or porous surfaces. The pigments can be used in powder coating compositions. They can be incorporated into plastic articles geared for the toy industry or the home. These pigments can be impregnated into fibers to impart new and esthetic coloring to clothes and carpeting. They can be used to improve the look of shoes, rubber and vinyl/marble flooring, vinyl siding, and all other vinyl products. In addition, these colors can be used in all types of modeling hobbies.

The above-mentioned compositions in which the compositions of this invention are useful are well known to those of ordinary skill in the art. Examples include printing inks, nail enamels, lacquers, thermoplastic and thermosetting materials, natural resins and synthetic resins. Some non-limiting examples include polystyrene and its mixed polymers, polyolefins, in particular, polyethylene and polypropylene, polyacrylic compounds, polyvinyl compounds, for example polyvinyl chloride and polyvinyl acetate, polyesters and rubber, and also filaments made of viscose and cellulose ethers, cellulose esters, polyamides, polyurethanes, polyesters, for example polyglycol terephthalates, and polyacrylonitrile.

For a well-rounded introduction to a variety of pigment applications, see Temple C. Patton, editor, The Pigment Handbook, volume II, Applications and Markets, John Wiley and Sons, New York (1973). In addition, see for example, with regard to ink: R. H. Leach, editor, The Printing Ink Manual, Fourth Edition, Van Nostrand Reinhold (International) Co. Ltd., London (1988), particularly pages 282–591; with regard to paints: C.H. Hare, Protective Coatings, Technology Publishing Co., Pittsburgh (1994), particularly pages 63–288. The foregoing references are hereby incorporated by reference herein for their teachings of ink, paint and plastic compositions, formulations and vehicles in which the compositions of this invention may be used including amounts of colorants. For example, the pigment may be used at a level of 10 to 15% in an offset lithographic ink, with the remainder being a vehicle containing gelled and ungelled hydrocarbon resins, alkyd resins, wax compounds and aliphatic solvent. The pigment may also be used, for example, at a level of 1 to 10% in an automotive paint formulation along with other pigments which may include titanium dioxide, acrylic lattices, coalescing agents, water or solvents. The pigment may also be used, for example, at a level of 20 to 30% in a plastic color concentrate in polyethylene.

In the cosmetic field, these pigments can be used in the eye area and in all external and rinse-off applications. Thus, they can be used in hair sprays, face powder, leg-makeup, insect repellent lotion, mascara cake/cream, nail enamel, nail enamel remover, perfume lotion, and shampoos of all types (gel or liquid). In addition, they can be used in shaving cream (concentrate for aerosol, brushless, lathering), skin glosser stick, skin makeup, hair groom, eye shadow (liquid, pomade, powder, stick, pressed or cream), eye liner, cologne stick, cologne, cologne emollient, bubble bath, body lotion (moisturizing, cleansing, analgesic, astringent), after shave lotion, after bath milk and sunscreen lotion.

For a review of cosmetic applications, see Cosmetics: Science and Wiley-Technology, 2nd Ed., Eds: M. S. Balsam and Edward Sagarin, Interscience (1972) and deNavarre, The Chemistry and Science of Cosmetics, 2nd Ed., Vols 1 and 2 (1962), Van Nostrand Co. Inc., Vols 3 and 4 (1975), Continental Press, both of which are hereby incorporated by reference.

In order to further illustrate the invention, various examples are being set forth below. In these examples, as well as throughout the balance of this specification and claims, all temperatures are in degrees Centigrade and all parts and percentages are by weight unless otherwise indicated.

EXAMPLE 1

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

After about 80 minutes, the pH was adjusted to 3 and a 39% aqueous solution of ferric chloride was introduced into the aqueous bismuth oxychloride crystal slurry at a rate of 1 ml per minute while simultaneously adding 20% aqueous sodium hydroxide at a rate of 3 ml/min in order to maintain the pH at that value.

After about 15 minutes, the resulting pigment was recovered and evaluated for light stability. This was done by first concentrating the crystals present in the aqueous phase of the slurry by settling and removing the supernatant. The crystals were then flushed into an organic phase which consisted of a ketone ester and aromatic solvents, followed by being dispersed in an organic soluble resin at a crystal content of 60% by weight. Thereafter the dispersed crystals were incorporated into an acrylic-melamine/formaldehyde baking enamel such that the amount of crystals in the enamel was 10% weight of the total resin solids in the enamel. The enamel dispersion was then sprayed on Bonderite 40 treated cold rolled and polished steel panels primed with a low film build cathodic electrodeposition primer. Wet on wet coats were applied so that the dried film thickness was in the range of about 0.0023 to 0.0028 cm (about 0.9 to 1.1 mils). This was followed by an acrylic melamine/formaldehyde clear coat of about 0.0038 to 0.005 cm (about 1.5 to 2 mils) dry film thickness. The panels were then baked for 30 minutes at 250° F. in a forced air oven.

An evaluation test was carried out by placing partly masked panels in a Cleveland chamber and exposing them to alternate cycles of 8 hours of xenon light and 4 hours of water condensation for one week. Changes in appearance of the panels were characterized by measuring the CIE L*a*b* values. This system is described in the text "The Measurement of Appearance", 2nd ed., Hunter and Harold, editors, John Wiley & Sons, 1987. The system involves measuring a lightness-darkness component designated L*, a red-green component designated a* and a yellow-blue component designated b*. The difference in color, designated DE* is calculated using the equation $$DE^* = [(DL^*)^2 + (Da^*)^2 + (Db^*)^2]^{1/2}$$

in which DL*, Da* and Db* represents the difference in L*, A* and b* values between the exposed and unexposed sections of the panel. The higher the value of DE*, the greater the change in appearance between the exposed and unexposed sections of the panel. Conversely, a lower DE* indicates increased light stability. A DE* of less than 1 is generally not apparent to the naked eye.

The DE* of a panel using the pigment of this example was less than 2. The DE* of a corresponding control panel prepared using a BiOCl pigment prepared in the same manner but without the hydrous iron oxide coating on it was 8.

A sample of the pigment was suspended in a nitrocellulose lacquer which was applied as a thin film to a conventional black and white drawdown card and dried. The film felt smooth to the touch and there was no apparent visible difference between the appearance of the film on the black portion of the card and the white portion.

For comparison purposes, a similar hydrous iron oxide coated BiOCl pigment was prepared except the BiOCl was not isolated from the reaction mixture before being coated and a continuous coating was formed. A sample was suspended in the same nitrocellulose lacquer at the same concentration as with the inventive pigment, and was applied as a thin film of the same thickness to the drawdown card and dried. The iron oxide had clumped and the film had a texture similar to sandpaper. There was a very apparent difference between the appearance of the film on the black portion of the card and the white portion.

EXAMPLE 2

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

After about 80 minutes, the pH was adjusted to 3 and a 39% aqueous solution of ferric chloride was introduced into the aqueous bismuth oxychloride crystal slurry at a rate of 1 ml per minute while simultaneously adding 20% aqueous sodium hydroxide at a rate of 3 ml/min in order to maintain the pH at that value. After about 15 minutes, the resulting pigment was recovered and dried at 120 degrees C.

The dried pigment was dispersed in an organic soluble resin at a crystal content of 60% by weight. Thereafter the dispersed crystals were incorporated into an acrylic-melamine/formaldehyde baking enamel such that the amount of crystals in the enamel was 10% weight of the total resin solids in the enamel. The enamel dispersion was then sprayed on Bonderite 40 treated cold rolled and polished steel panels primed with a low film build cathodic electrodeposition primer. Wet on wet coats were applied so that the dried film thickness was in the range of about 0.0023 to 0.0028 cm (about 0.9 to 1.1 mils). This was followed by an acrylic melamine/formaldehyde clear coat of about 0.0038 to 0.005 cm (about 1.5 to 2 mils) dry film thickness. The panels were then baked for 30 minutes at 250° F. in a forced air oven.

An evaluation test was carried out as described in Example 1. The DE* of a panel using the pigment of this example was 1.8. The DE* of a corresponding control panel prepared using a BiOCl pigment prepared in the same manner but without the hydrous iron oxide coating on it was 8.

EXAMPLE 3

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

After about 80 minutes, the pH was adjusted to 3 and a 39% aqueous solution of ferric chloride in an amount of about 5% was introduced into the aqueous bismuth oxychloride crystal slurry followed by adding 20% aqueous sodium hydroxide at a rate of 1 ml/min in order until the pH was 10. After being maintained at that pH for about 15 minutes, the resulting pigment was recovered and dried at 120 degrees C. The dried pigment can be formulated into Powder Eye Shadow as follows:

The following materials are thoroughly blended and dispersed:

| Ingredients | wt parts |
| --- | --- |
| Mearltalc TCA ® (Talc) | 18 |
| Mearlmica ® SVA (Mica) | 20 |

| Ingredients | wt parts |
| --- | --- |
| Magnesium Myristate | 5 |
| Silica | 2 |
| Cloisonné ® Red 424C (red TiO$_2$-coated mica) | 20 |
| Cloisonné ® Violet 525C (violet TiO$_2$-coated mica) | 13 |
| Cloisonné ® Nu-Antique Blue 626CB (TiO$_2$-coated mica/iron oxide-coated mica) | 2 |
| Cloisonné ® Cerise Flambé550Z (iron oxide-coated mica) | 2 |
| Preservatives & Antioxidant | q.s. |

Then 7 parts of octyl palmitate and 1 part of isostearyl neopentanoate are heated and mixed until uniform, at which time the resulting mixture is sprayed into the dispersion and the blending continued. The blended material is pulverized and then 5 parts of Cloisonne Red 424C and 5 parts of the coated BiOCl added and mixed until a uniform powder eye shadow is obtained.

EXAMPLE 4

A sufficient quantity of concentrated hydrochloric acid was introduced into a demineralized water reservoir to bring the pH of the resulting reservoir to about 1. After the reservoir had been heated to about 70° C., 400 milliliters of an aqueous solution containing hydrochloric acid and 0.2 g/ml of bismuth nitrate was pumped into the reservoir at a rate of 5 ml/minute. Simultaneously, a 20% aqueous sodium hydroxide solution was added to the reservoir in order to neutralize the acid which was being formed during the hydrolysis reaction.

After about 80 minutes, the pH was adjusted to 3 and a 39% aqueous solution of ferric chloride in an amount of about 5% was introduced into the aqueous bismuth oxychloride crystal slurry followed by adding 20% aqueous sodium hydroxide at a rate of 1 ml/min in order until the pH was 10. After being maintained at that pH for about 15 minutes, the resulting pigment was recovered and dried at 120 degrees C. The dried pigment can be formulated into Lipstick as follows.

The following amounts of the listed ingredients are placed into a heated vessel and the temperature raised to 85±3° C.

| | wt parts |
| --- | --- |
| Candelilla Wax | 2.75 |
| Carnauba Wax | 1.25 |
| Beeswax | 1.00 |
| Ceresine Wax | 5.90 |
| Ozokerite Wax | 6.75 |
| Microcrystalline Wax | 1.40 |
| Oleyl Alcohol | 3.00 |
| Isostearyl Palmitate | 7.50 |
| Isostearyl Isostearate | 5.00 |
| Caprylic/Capric Triglyceride | 5.00 |
| Bis-Diglycerylpolyalcohol Adipate | 2.00 |
| Acetylated Lanolin Alcohol | 2.50 |
| Sorbitan Tristearate | 2.00 |
| Aloe Vera | 1.00 |
| Castor Oil | 37.50 |
| Red 6 Lake | 0.25 |
| Tocopheryl Acetate | 0.20 |
| Phenoxyethanol, Isopropylparaben, and butylparaben | 1.00 |
| Antioxidant | q.s. |

A mixture of 13 parts of the coated BiOCl and 1 part of kaolin are added and mixed until all of the BiOCl is well dispersed. Fragrance is added as desired and mixed with stirring. The resulting mixture is poured into molds at 75±5° C., allowed to cool and flamed into lipsticks.

Various changes and modifications can be made in the process and products of this invention without departing from the spirit and scope thereof. The various embodiments which were disclosed herein were for the purpose of further illustrating the invention but were not intended to limit it.

What is claimed is:

1. An effect pigment which comprises bismuth oxychloride crystals having a surface coating of hydrous iron oxide.

2. The effect pigment of claim 1 in which the surface coating is about 0.1 to 70 weight percent of the total weight of the coated crystals.

3. The effect pigment of claim 2 in which the surface coating is about 10 to 40 weight percent of the total weight of the coated crystals.

4. The effect pigment of claim 3 in which the surface coating is discontinuous and the effect pigment is dry.

5. The effect pigment of claim 2 in which the surface coating is discontinuous and the effect pigment is dry.

6. The effect pigment of claim 1 in which the surface coating is discontinuous and the effect pigment is dry.

7. A method of producing a bismuth oxychloride pigment having improved light stability which comprises combining a soluble bismuth salt and chloride ions in an aqueous medium under hydrolyzing conditions to form an aqueous dispersion of bismuth oxychloride crystals, adding a hydrolyzable iron salt to the aqueous dispersion and hydrolyzing the iron salt to form an hydrous iron oxide coating on the bismuth oxychloride.

8. The process of claim 7 in which the amount of hydrolyzable iron salt is about 0.1 to 70 weight percent based on the weight of the bismuth oxychloride.

9. The process of claim 8 in which the amount of hydrolyzable iron salt is about 10 to 40 weight percent based on the weight of the bismuth oxychloride.

10. The process of claim 9 in which the hydrous iron oxide coated bismuth oxychloride is dried.

11. The process of claim 8 in which the hydrous iron oxide coated bismuth oxychloride is dried.

12. The process of claim 7 in which the hydrous iron oxide coated bismuth oxychloride is dried.

13. In a composition pigmented by a bismuth oxychloride effect pigment, utilizing the bismuth oxychloride effect pigment of claim 1 as said pigment.

14. In a composition pigmented by a bismuth oxychloride effect pigment, utilizing the bismuth oxychloride effect pigment of claim 2 as said pigment.

15. In a composition pigmented by a bismuth oxychloride effect pigment, utilizing the bismuth oxychloride effect pigment of claim 3 as said pigment.

16. In a paint or ink composition including a pigment, the improvement which comprises said pigment being the bismuth oxychloride effect pigment of claim 1.

17. In a plastic composition including a pigment, the improvement which comprises said pigment being the bismuth oxychloride effect pigment of claim 1.

18. In a cosmetic composition including a pigment, the improvement which comprises said pigment being the bismuth oxychloride effect pigment of claim 1.

* * * * *

UNITED STATES PATENT AND TRADEMARK OFFICE
CERTIFICATE OF CORRECTION

PATENT NO. : 6,579,357 B1 Page 1 of 1
DATED : June 17, 2003
INVENTOR(S) : Paul Cao It is certified that error appears in the above-identified patent and that said Letters Patent is hereby corrected as shown below:

Column 4,
Line 36, after "Science and" delete "Wiley-".
Line 37, after "Sagarin," insert -- Wiley- --.

Signed and Sealed this

Twenty-fourth Day of February, 2004

JON W. DUDAS
*Acting Director of the United States Patent and Trademark Office*